(12) United States Patent
Ollivier (10) Patent No.: US 9,717,902 B2
(45) Date of Patent: Aug. 1, 2017

(54) PACING LEAD FOR A LEFT CAVITY OF THE HEART, IMPLANTED IN THE CORONARY SYSTEM

(71) Applicant: SORIN CRM SAS, Clamart (FR)

(72) Inventor: Jean-François Ollivier, Gif sur Yvette (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 14/688,121

(22) Filed: Apr. 16, 2015

(65) Prior Publication Data

US 2015/0217110 A1    Aug. 6, 2015

Related U.S. Application Data (63) Continuation of application No. 13/960,640, filed on Aug. 6, 2013, now Pat. No. 9,014,822, which is a continuation of application No. 13/300,451, filed on Nov. 18, 2011, now Pat. No. 8,521,306.

(30) Foreign Application Priority Data

Nov. 19, 2010  (FR) ..................... 10 59521

(51) Int. Cl.
    *A61N 1/05*    (2006.01)
(52) U.S. Cl.
    CPC ........... *A61N 1/0587* (2013.01); *A61N 1/056* (2013.01); *A61N 1/0573* (2013.01); *A61N 2001/0585* (2013.01)
(58) Field of Classification Search
    CPC .......... A61N 1/05; A61N 1/0558; A61N 1/08; A61N 1/36017; A61N 1/375; A61N 1/059; A61N 1/057; A61B 18/1492; A61B 2562/222; A61B 2562/227; A61B 5/04

See application file for complete search history.

(56) References Cited

U.S. PATENT DOCUMENTS

| | | | |
|---|---|---|---|
| 5,370,684 | A | 12/1994 | Vallana et al. |
| 5,387,247 | A | 2/1995 | Vallana et al. |
| 6,385,492 | B1 | 5/2002 | Ollivier et al. |
| 7,254,450 | B2 | 8/2007 | Christopherson et al. |
| 7,483,753 | B2 | 1/2009 | Ollivier et al. |
| 2003/0167082 | A1 | 9/2003 | Ollivier et al. |

(Continued)

FOREIGN PATENT DOCUMENTS

| | | |
|---|---|---|
| EP | 1 374 945 | 1/2004 |
| EP | 1 938 861 | 7/2008 |

*Primary Examiner* — Deborah Malamud
(74) *Attorney, Agent, or Firm* — Foley & Lardner LLP (57) ABSTRACT

A pacing lead for a left cavity of the heart, implanted in the coronary system. The lead includes a lead body with a hollow sheath of deformable material, having a central lumen open at both ends, and at least one telescopic microcable of conductive material. The microcable slides along the length of the lead body and extends beyond the distal end thereof. The part emerging beyond the distal end is an active free part comprising a plurality of distinct bare areas, intended to come into contact with the wall of a target vein of the coronary system, so as to form a network of stimulation electrodes electrically connected together in parallel. The microcable further comprises, proximally, a connector to a generator of active implantable medical device such as a pacemaker or a resynchronizer.

20 Claims, 4 Drawing Sheets

(56) References Cited

U.S. PATENT DOCUMENTS

| | | |
|---|---|---|
| 2007/0106357 A1* | 5/2007 | Denker et al. ............... 607/116 |
| 2008/0082136 A1 | 4/2008 | Gaudiani |
| 2008/0177343 A1 | 7/2008 | Dal Molin et al. |
| 2009/0088827 A1 | 4/2009 | Tockman et al. |
| 2009/0157136 A1 | 6/2009 | Yang et al. |
| 2010/0114284 A1 | 5/2010 | Doerr |

* cited by examiner

PACING LEAD FOR A LEFT CAVITY OF THE HEART, IMPLANTED IN THE CORONARY SYSTEM

CROSS-REFERENCE TO RELATED PATENT APPLICATIONS

The present application is a continuation of U.S. application Ser. No. 13/960,640, entitled "Pacing Lead for a Left Cavity of the Heart, Implanted in the Coronary System," filed Aug. 6, 2013, now U.S. Pat. No. 9,014,822, which is a continuation of U.S. application Ser. No. 13/300,451, entitled "Pacing Lead for a Left Cavity of the Heart, Implanted in the Coronary System," filed Nov. 18, 2011, now U.S. Pat. No. 8,521,306, which claims the benefit of French Application No. 1059521, entitled "Pacing Lead for a Left Cavity of the Heart, Implanted in the Coronary System," filed Nov. 19, 2010, each of which is hereby incorporated by reference in their entireties.

BACKGROUND

The present invention relates to "active implantable medical devices" as defined by the 20 Jun. 1990 Directive 90/385/EEC of the Council of the European Communities, more particularly to devices that continuously monitor a patient's heart rhythm and deliver to the heart, if necessary, electrical pulses for stimulation, resynchronization, cardioversion and/or defibrillation, and even more particularly to cardiac pacing leads intended to be implanted in the coronary network of the heart for stimulation of a left ventricular or atrial cavity.

For the right cavities of a patient's heart, it is generally sufficient to implant endocardial leads through the right peripheral venous network. The implantation of permanent leads in a left heart cavity, however, involves significant operational risks, for example, the passage of bubbles to the vascular network of the brain located downstream of the left ventricle. For this reason, when the left cavity has to be stimulated, most often a lead is not introduced to the cavity to be stimulated, but rather into the coronary system, with the lead having an electrode that is guided to the left ventricle or left atrium and applied against the wall of the epicardium, as appropriate.

A lead of this type is, for example, the Situs LV model, marketed by Sorin CRM S.A.S. (Clamart, France) and described in EP 0993840 A1 and its US counterpart U.S. Pat. No. 6,385,492 (both assigned to Sorin CRM S.A.S., previously known as ELA Medical). Such a lead is introduced through the coronary sinus opening into the right atrium, by an endocardial approach. The lead is then guided and pushed along the coronary vein network to the chosen stimulation site. This intervention is very difficult, given the peculiarities of the venous network and its access paths, including the passage through valves and tortuosities, as well as experiencing a gradual reduction in diameter of the vein as the lead is advanced along the selected coronary vein. Once the target vein is reached, the surgeon must then, first of all, ensure the mechanical stability of the lead into the vein.

Another problem is the difficulty of finding a good stimulation site, to obtain good electrical contact between the stimulating electrode and the tissue of the epicardium, and maintain this contact over time.

In addition, the surgeon must ensure that the chosen stimulation point does not generate phrenic nerve stimulation.

To overcome these difficulties, it was proposed to have multiple electrodes along the lead body to increase the chances of an acceptable compromise, by possibly giving the lead body a particular conformation. The surgeon can choose from among the various electrodes present on the lead body to find the one that provides the best efficiency from the electrical and hemodynamic points of view. One such multiple electrode lead is described in EP 1938861 A1 and its US counterpart US Patent Publication No. 2008/0177343 (both assigned to Sorin CRM S.A.S previously known as ELA Medical). These leads allow in particular to implement the concept of "electronic repositioning" to direct or redirect the electrical field between different electrodes arranged along the pacing lead of the left cavity and/or with an electrode of the pacing lead of the right cavity. The technology allows managing the micro-movements or changes in the hemodynamic behavior (reverse modeling) simply by reprogramming the generator via telemetry through the skin, without major surgery.

The counterpart of this solution is an increasing complexity of the structure of the lead, an increase of the number of electrodes causing an increase in the number of components, and therefore of electrical connections, or the use of multiplexing circuits for selecting the various electrodes present on a same lead.

US Patent Publication No. 2009/157136 A1 describes a technique of searching for an optimal pacing site using a temporary mapping catheter to be introduced into the coronary sinus. This catheter is a flexible tube open at both ends, and has, optionally, a guide wire. It is equipped with electrically independent multiple distal electrodes, and at its proximal side, a connector for connection to a data acquisition system for identifying the best stimulation site with an algorithm based on cardiac motion.

A permanent conventional multi-electrode lead, having for example a standard diameter of 4.5 to 6 French, is then placed at the selected location, using either the guide wire and a standard over the wire ("OTW") technique, or the tube, of the temporary catheter.

Another recent development for a left ventricle pacing lead is to reduce the diameter of the implantable part in the coronary system, to a diameter of 4 French (1.33 mm).

The size of the lead body is indeed a factor directly related to the capacity of controlled guiding of the lead in the coronary venous system, so as to select particular stimulation sites located in some specific collateral veins. These sites are reached by means of a vein sub-selection catheter used to place a guiding stylet at the chosen site. Once the vein is selected and the stylet is placed, the surgeon advances the lead body which slides on the stylet, the latter acting as a guide wire of small diameter axially guiding the lead body to the chosen location (an OTW technique).

The size of the lead body is indeed a factor directly related to the capacity of controlled guiding of the lead in the coronary venous system, so as to select particular stimulation sites located in some specific collateral veins. These sites are reached by means of a vein sub-selection catheter used to place a guiding stylet at the chosen site. Once the vein is selected and the stylet is placed, the surgeon advances the lead body which slides on the stylet, the latter acting as a guide wire of small diameter axially guiding the lead body to the chosen location (an OTW technique).

These solutions however have two notable limitations: (1) The fineness of the lead, whose diameter does not allow to access the deepest collateral veins: for example, the Situs lead referenced above has a diameter of 2.2 mm (6.6 French) and requires a 7 French diameter introducer, and (2) The correct positioning and good maintaining of the electrical contact of the electrode against the tissue to cause stimulation.

The above techniques of multi-electrode leads and electronic repositioning make possible to (more or less appropriately) overcome the second limitation, however they increase the first limitation, to the extent that the multiplication of electrodes and of the internal conductors or components necessarily implies an increase in the diameter of the lead body which reduces its flexibility, making it difficult or even impossible to ensure passage through the tortuous coronary venous system.

The solutions heretofore known are therefore always a compromise between these two constraints.

SUMMARY

It is, therefore, an object of the invention to provide a left heart cavity pacing lead having a very small diameter and an active part for stimulating multiple areas of the epicardium.

It is another object of the invention to propose such a lead having a simple structure that is inexpensive to manufacture, reliable, and avoids problems related to the design and use of multiple electrode leads.

Broadly, the present invention provides a coronary sinus lead that, once the site of stimulation is selected and assessed, ensures optimum and sustainable stability of the stimulating electrode on this site.

The present invention also allows separating the problem of the stability from that of the electro-hemodynamic performance. Indeed, as it will be seen, the stability is ensured by the distal end of the lead (having a predefined shape such as a screw made of silicone), while the stimulation is provided by a telescopic microcable equipped with one or more continuous or disjointed pacing areas.

In particular, if it can be ensured that the electrode remains in place, regardless of at what site or place it was originally implanted, further movements of the lead are prevented, stability is achieved, and it is no longer necessary to overcome the consequences of such a displacement by complex techniques, such as electronic repositioning or the selection among multiple electrodes.

Essentially, one embodiment of the invention is for a pacing lead, intended to be implanted in a coronary network vein for the stimulation of a left cavity of the heart, including the elements known from the US Patent Publication No. 2009/157136 A1 cited above, that is to say comprising a telescopic microcable in a conductive material, comprising at its distal end an active free part comprising a plurality of distinct bare areas, these bare areas being intended to come into contact with the wall of a target vein of the coronary network, so as to form a network of stimulation electrodes. The cable further comprises, on its proximal side, means for coupling the network of stimulation electrodes to a generator of an active implantable medical device, such as a pacemaker or a resynchronizer. Such a coupling means may be, for example, a terminal that can be inserted into a standard connector head of the implantable device, or is otherwise electronically connected, directly or indirectly, to a pulse generator output of an implanted action medical device.

In a preferred embodiment, the cable is a telescopic microcable the diameter of which is between 0.5 and 2 French, made of a plurality of microwires twisted together, in which at least some of the plurality of strands incorporate either a core having a radiopaque material, such as platinum-iridium or tantalum wrapped in a sheath of mechanically durable material such as NiTi or stainless steel, or vice versa.

In addition, the distinct bare areas are preferably bare areas of the microcable, and form a network of stimulation electrodes electrically connected together.

The small diameter microcable (more typically from 1 to 2 French) is advantageously used to catheterize veins of very small diameter, which have not before been exploited due to the larger size of the previously known permanent coronary probes.

The dual constraint mentioned above is thus overcome by the microcable structure, which in a preferred embodiment, is a structure without an internal lumen, and with several microwires twisted together, a configuration capable of both ensuring endurance against cardiac movements and resistance to the stresses during implantation.

This microcable is suitable to be introduced into the coronary network via a permanent carrier lead (e.g., with no particular mapping capacity), previously placed into the vein.

The small diameter is the essential characteristic that divides the surface of the monopolar electrode through multiple windows arranged along the body of the microcable. This allows permanent stimulation of a large area of the heart wall via this monopolar microlead. For diameters of between 1 and 2 French, it would not be possible to provide an individual isolation of each strand that can withstand the abrasion constraints between strands.

Various embodiments can be envisaged.

In one embodiment, the present invention provides a pacing lead, intended to be implanted in a coronary network vein for the stimulation of a left cavity of the heart, comprising a telescopic microcable made of a conductive material, having at its distal end an active free part comprising a plurality of distinct bare areas. These distinct bare areas are intended to come into contact with the wall of a target vein of the coronary network, so as to form a network of stimulation electrodes electrically connected together. The microcable further comprises, at its proximal end, means for coupling to a generator of an active implantable medical device, such as a pacemaker or a resynchronizer.

Preferably, the distal end of the microcable comprises a two- or three-dimensional pre-formed shape, having external dimensions in a rest state that are typically included within a cube having dimensions of between 1 to 90 mm per side. The microcable can thus be implanted alone, and held in place by its own particular distal pre-formed shape. In this embodiment, the placement in the vein is carried out by conventional means such as catheter/sub-catheter or brain access catheter.

Another embodiment of the present invention is directed to a system comprising a microcable and a lead body having a hollow sheath made of a deformable material, a central lumen open at both ends and in which the microcable is positioned, ready to slide by extending along the entire length of the lead body and beyond its distal end, such that the part of the microcable emerging beyond the distal end of the lead body is the active free part of the microcable.

To ensure maintaining the position of the microcable in the vein, the distal end of the lead body may be provided with a retaining means, including at least one relief formed on the lead body. Preferably, the at least one relief includes an helical relief with a thread wrapping around the lead body, having a locally increased diameter compared to that of the lead body itself, including a diameter greater than or equal to 7 French.

The lead body preferably includes a main part distally extended by a transition portion having a smaller diameter than that of the main part, including a diameter of the main part lower or equal to 6 French and a diameter of the transition part less than or equal to 5 French.

In yet another embodiment, the lead comprises a common lead body and a plurality of separate telescopic microcables, each of which is housed in the lead body and is slidable therein, the respective active free parts of the different microcables emerging from the lead body in separate locations, longitudinally spaced along the lead body. Preferably, in all cases, the diameter of each microcable is typically between 0.5 and 2 French, with an exposed total surface of the distinct bare region(s) of the active free part of the microcable of at least 1 mm$^2$, more preferably between 4 and 6 mm$^2$ and a length of the active free part being adjustable between 1 and 200 mm.

In one embodiment, the active free part of the microcable comprises a plurality of distinct bare regions that successively extend along the active free part of the microcable. More preferably, these distinct bare areas are separated from each other by portions of tube made of an electrically non-conductive material, wrapping and sheathing the microcable between two consecutive bare areas. The bare areas also may bear tubular rings made of an electrically conductive material, which are crimped on the microcable. The electrically conductive material of the tubular rings inserted on the microcable is preferably made of a radio-opaque material.

In another embodiment, the microcable includes a stranded structure coated with an insulating material, including parylene, in which the distinct bare areas are formed by ablation forming openings in the insulating material along the microcable. Preferably, titanium nitride is then deposited on the distinct bare areas thus formed.

Preferably, the length in the longitudinal direction of each bare area is typically selected to be between 0.5 and 10 mm.

The microcable is advantageously formed of a plurality of strands twisted together, in which at least some strands incorporate either a core made of a radiopaque material, such as platinum-iridium, wrapped in a sheath of a mechanically durable material such as NiTi or stainless steel, or vice versa.

In another embodiment of the invention, the active free part of the microcable has at least an helically bare area extending along the active free part. The microcable can notably include, on at least one portion of the active free part, a strand formed of a plurality of twisted strands having a surface with a corresponding plurality of helical bare regions, isolated from each other in the circumferential direction by helical coatings of an electrically non-conductive material.

Advantageously, a lead in accordance with the present invention has a very small diameter, able to exploit the entire length of the vein and make an optimal use of all the veins present in the basal zone, especially to avoid the risk of phrenic nerve stimulation, which generally increases when the lead is too distal. In addition, the left heart pacing lead ensures an excellent and durable electrical contact with the tissues to be stimulated. A further advantage of the lead is that it increases or expands the areas of stimulation, allowing (as opposed to traditional leads) stimulation of multiple areas of the epicardium, thereby improving the chances of an optimal resynchronization.

BRIEF DESCRIPTION OF THE DRAWINGS

Further features, characteristics, and advantages of the present invention will become apparent to a person of ordinary skill in the art from the following detailed description of preferred embodiments of the present invention, made with reference to the annexed drawings, in which.

DETAILED DESCRIPTION

With reference to the drawings, FIGS. 1-6, preferred embodiments of a device in accordance with the present invention will now be described.

Figure 1:
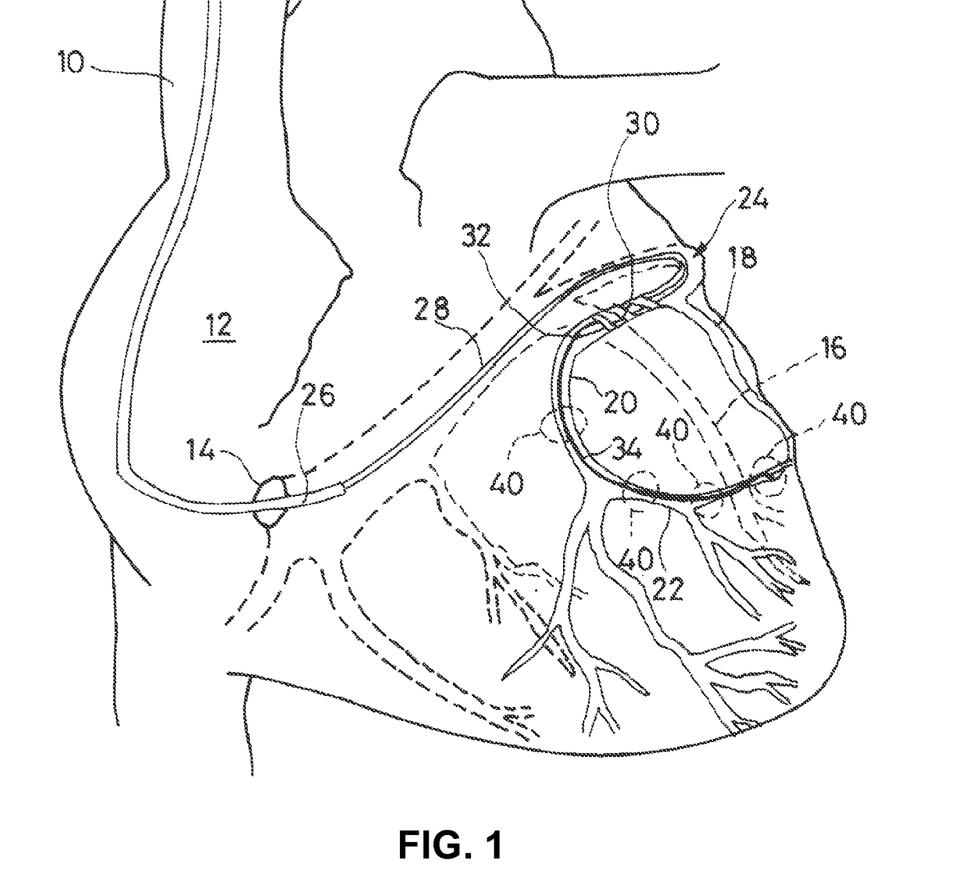
FIG. 1 shows the heart and its coronary venous network in which a lead according to the invention is implanted.

FIG. 1 generally illustrates the myocardium, in which a lead 26 for pacing of the left ventricle according to the present invention has been introduced. Lead 26 is endocardially implanted in the venous coronary network via the superior vena cava 10, the right atrium 12 and the entry 14 of the venous coronary sinus. The venous coronary system then develops into several branches, including the postero-lateral vein 16, the lateral vein 18, the great cardiac vein 20 and the antero-lateral vein 22.

Reference 24 generally designates the lead of the invention, which includes a lead body having a main part 26 (e.g., a 6 French diameter) entering into the coronary sinus 14, extended by a transition portion 28 of the same conformation but of smaller diameter (e.g. 4.8 French) to allow better penetration into the coronary venous system.

This lead body is formed of a tubular hollow sheath made of a deformable material, such as silicone or polyurethane, defining a central lumen extending from one end to the other of lead body.

At the distal end, the lead body is provided with retaining means 30 to allow its mechanical support in the vein. This retaining means may be, for example, a screw as described in EP 1374945 A1 and its counterpart U.S. Pat. No. 7,483,753 (both assigned to Sorin CRM S.A.S. previously known as ELA Medical), equipped with a helical thread having a maximum outer diameter of about 7 French. See FIG. 6. This retaining means is of the same type as that used by the aforementioned Situs LV model lead. The screw thread is molded in a cylindrical element terminating the transition part 28 of the lead body, the whole assembly preferably being molded in one piece in a material such as a silicone rubber, or a similar material that is not traumatic and ensures good biocompatibility. Moreover, the distal end of the lead body, provided with the retaining means 30 is open at lumen end 32, the outlet including a sealing means (not shown, but of a conventional design), for example, a penetrable silicone plug to prevent any backflow of blood inside the lead body in both the absence and the presence of an element introduced into the central lumen of the lead body.

This lead body is implanted according to a conventional OTW technique by use of a very thin stylet forming a guide wire, provided at its distal end with a flexible end for not being traumatic and for allowing its direct introduction into the vessels of the coronary system without risk of perforation.

Previously, the surgeon has a main catheter allowing him/her to access at the end of the coronary sinus and a sub-selection catheter to choose, under fluoroscopy, the path of the venous system that allows achieving the target vein corresponding to the chosen stimulation site.

The surgeon then introduces the guide wire into the catheter, and pushes it to advance it in the coronary venous system in order to select a particular collateral vein. Once the collateral vein is selected, the surgeon pulls on the guide wire for the lead body (the guide wire passes through the orifice 32 which is normally closed by the penetrable plug). The surgeon then drags and moves the lead body on the guide wire, which axially guides the lead body to the chosen location. Once the lead body is at the final position in the chosen vein, the surgeon gives the lead body an additional motion of rotation, which ensures, by screwing the thread of the retaining means 30, the further progression of the lead body of a few millimetres with a corresponding reinforcement of the anchoring of the lead body into the vein.

Typically, the lead body as described above (having a well-known and conventional structure) is extended by a telescoping microcable presenting the active part 34 of the lead (possibly in addition to a pre-existing active stimulation electrode, arranged on the lead). Preferably, the microcable has a diameter of about 0.5 to 2 French and extends over a length of 1 to 200 mm beyond the outlet 32 of the distal end of the lead body.

Once the lead body is implanted by the method indicated above and after removal of the guidewire, the microcable is then inserted into the lead body at its proximal end. It is pushed along the length of the lead body to emerge from the outlet 32, then is deployed beyond the outlet 32 so as to advance, under fluoroscopy in the collateral veins up to the desired position. It is thus possible to reach and stimulate areas of the coronary venous system previously inaccessible with the prior known leads.

The active part 34 of the microcable (i.e., its emerging part) has a plurality of distinct bare parts forming a succession of individual electrodes, together constituting an array of electrodes connected in series forming multiple stimulation points. For example, in FIG. 2, active part 34 includes, in addition to the distal electrode 36, a plurality of ring electrodes 38 arranged at regular intervals along the length of the active portion 34. This allows more opportunities for points 40 to make contact with the wall of the vein and thus to ensure a multi-zone distribution of the stimulation energy at several points of the epicardium and therefore of the left ventricle.

Figures 2, 3:
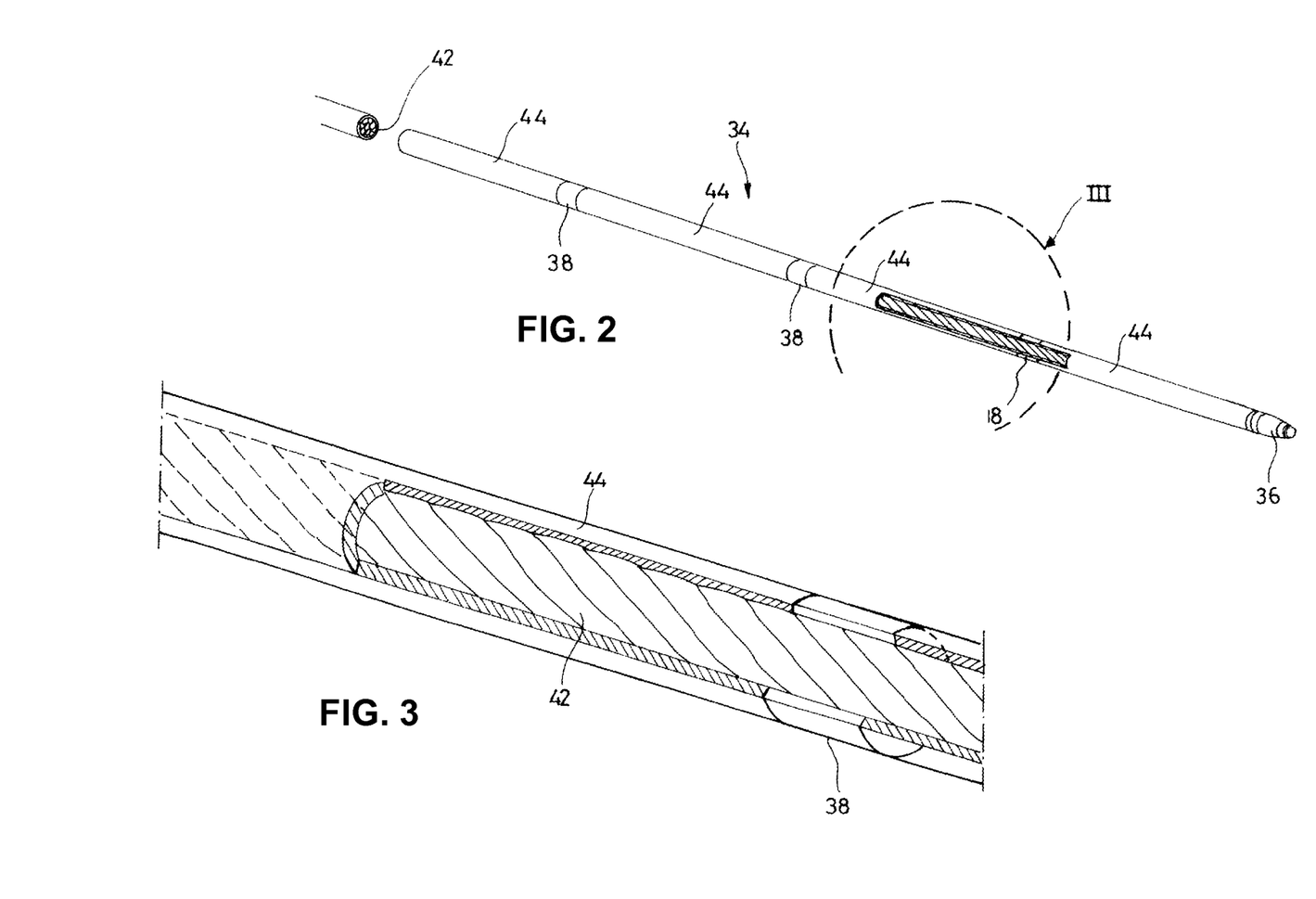
FIG. 2 illustrates an active part of a microcable of a first embodiment of the lead of the present invention.
FIG. 3 is an enlarged view of the detail marked III in FIG. 2.

FIGS. 2 and 3 illustrate a first embodiment of an active part (the one linked to the emerging part of microcable) of the lead of the invention. The core of active portion 34 is formed by microcable 42, on which insulating tubes 44 and short conducting electrodes 38 are successively and alternately threaded. Microcable 42 is terminated by distal electrode 36. The microcable 42 is advantageously made of a nitinol (NiTi alloy) core, a material whose main advantage is its extreme fatigue endurance. Preferably, the microcable structure has a plurality of strands in which each strand consists of a core of platinum-iridium coated with a thickness of nitinol (or vice versa). The system is then possibly coated either by a thin layer of parylene (e.g., of C type), or by a polyurethane tube. In either case, openings of varying complexity are arranged along the microcable, for example, by plasma ablation, to form the electrically active areas 36, 38. To improve the electrical performances, these areas may further be coated, for example by titanium nitride.

These types of microcables are available, for example, from Fort Wayne Metals Company Inc., Fort Wayne, USA, and heretofore have been used in the medical field, notably for defibrillation conductors —but in a different arrangement of material. In these prior known applications, the structure is a multi-wire structure in which each strand includes a core of silver (to improve conductivity) coated with a stainless steel thickness. These microstructures, isolated or not, are then incorporated into a multi-lumen lead body, the construction of which is classic and well known.

The benefits of the microcable structure described above lie in the fact that the less mechanically enduring elements (platinum-iridium or silver) are encapsulated directly in (or are coated around) the nitinol sheath. The consequences of a possible fracture of the strands are thus minimized.

Alternatively, it is possible to have a strand of platinum-iridium in the center of a 1×7-type multi-wire structure, the most fragile strand then being entwined by the most durable external strands.

Finally, platinum-iridium can be replaced by any radio-opaque material such as tantalum, and nitinol can be replaced with materials having a lower, but still sufficient, endurance performance, or a less expensive material such as stainless steel MP35N, commonly used in the manufacture of standard conductors.

Insulating tubes 44 extending between electrodes 36, 38 are preferably tubes made of polyurethane (PU), glued on the microcable with a PU-type glue. The fluidity of the glue, combined with the crevices formed by the twist of the microcable, ensures an optimum link between the PU tube and the microcable.

Platinum electrodes 36 and 38 are preferably crimped directly onto the microcable. The small thickness of the electrode, combined with the ductility of platinum, enhances the quality of the electrical contact without altering the microcable. On the other hand, the short length of the electrodes (e.g., 0.5 to 10 mm) significantly limits their impact on the overall mechanical behaviour of the system, which is mostly dictated by the microcable.

The individual surface of each electrode is about $0.5\ mm^2$, making it possible to distribute a large number (e.g., up to twelve over a length of 1 to 200 mm in the longitudinal direction) without exceeding a combined total surface of 6-8 $mm^2$.

Due to the low cumulative active surface area, the advantages of a "high current density" lead in terms of both physiological efficacy of stimulation and lower energy consumption are provided, while at the same time maximizing the chances of a physical, and thus electric, contact of the conductive surface (electrodes 36 and 38) of active portion 34 with the excitable tissues, due to an increase in the number of electrodes.

Moreover, the alternation of conductive and insulating zones combined with the telescopic properties of the system allows for an improved managing of the risk of phrenic stimulation. Indeed, if for a given position, the phrenic nerve is included in the electric field, it is possible to slide the microcable in the lead body to position it in a remote area far from the phrenic nerve and thus to escape this parasite stimulation.

The configuration as described above allows separating the two problems of placement of the lead in the coronary venous system and those related to the multiplication of the stimulation points. Indeed, the mechanical fixing and maintaining of the lead is provided upstream by the lead body itself and by the retaining means 30, while the multiplication of stimulation points is provided by the electrode array disposed along the telescopic microcable, which allows stimulating a large area chosen independently of the usual constraints of accessibility and stability.

In addition, to promote contact with the tissues, multiple types of preformed shapes are possible for the distal end of microcable, including, without limitation:

A sequence of bends with variable radius in a same plane;
Sequence of bends with variable radius in a series of separate planes;
Three-dimensional strongly curved trajectory, without any base plane, for example, of the pigtail type;
The external dimensions of the pre-formed shape in the rest state being included in a cube having a dimension of from 1 to 35 mm per side.

This particular configuration allows considering a particular variant of the implantation of the microcable alone (e.g., without a lead), it being then held in place by its very distal pre-formed shape.

In this embodiment, the placement in the vein is carried out by conventional catheter/sub-catheter means or brain access catheter.

Figure 4:
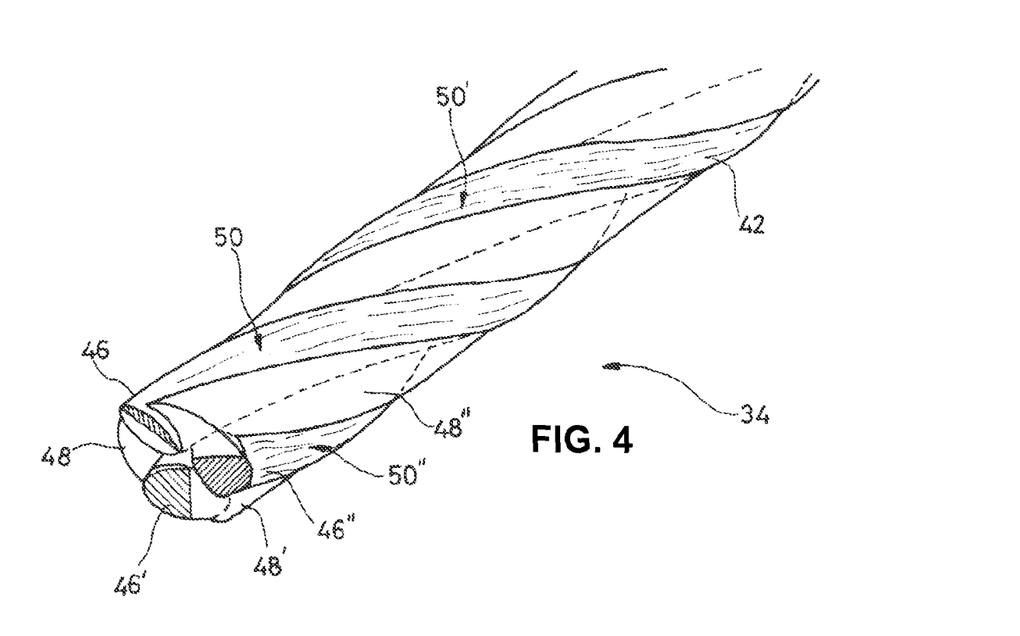
FIG. 4 is an enlarged view of an active part of the lead of a second embodiment of the invention.

FIG. 4 illustrates a second embodiment of an active part of the lead of the present invention. In this embodiment, the strand formed by the wires 46, 46', 46'' of the microcable has applied on it an insulating coating of isolating PU adhesive 48, 48', 48'', but on a smaller diameter than the overall outside diameter of the strand so as to reveal, in reserve, conductive surfaces 50, 50', 50'' (uncoated surfaces) of helical shape. The active area of the active surface 34 is thus a triple helix shape 50, 50', 50'' on the periphery of the microcable, on all or part of the length of the active region 34.

This solution makes it possible to "stretch" the surface in the longitudinal direction of stimulation, without increasing the total area of electrode.

Figure 5:
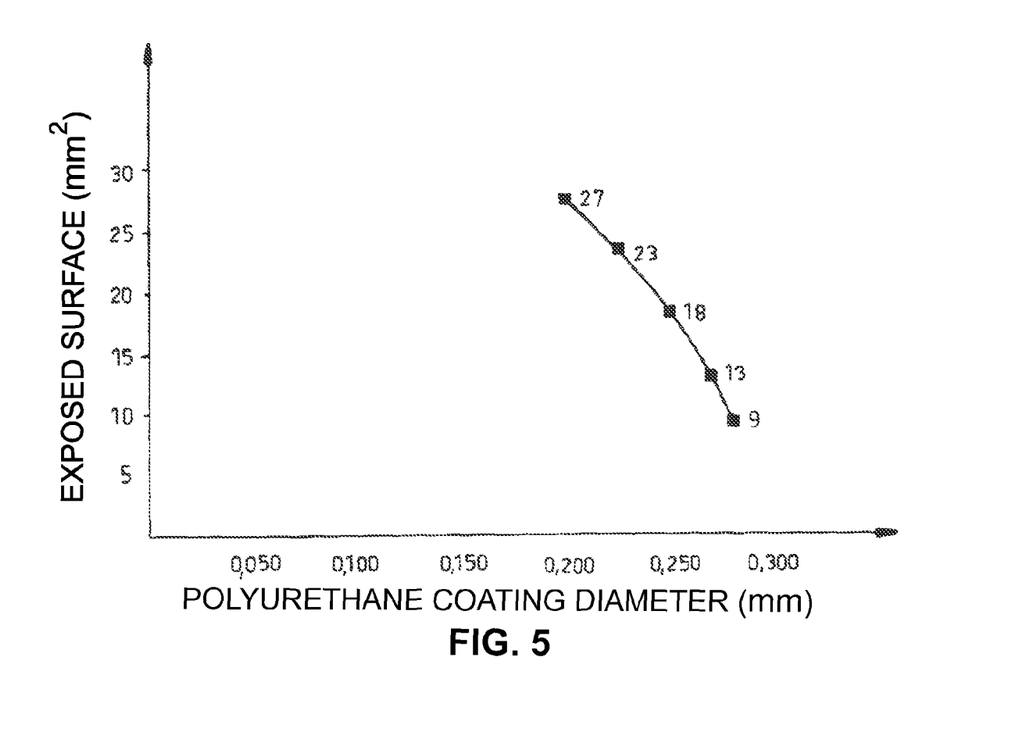
FIG. 5 is a graph representing a method to adjust the exposed active area by an appropriate selection of the diameter of the insulation coating on the active part of the lead illustrated in FIG. 4.

With reference to FIG. 5, the graph shown of the polyurethane coating diameter (mm) against the exposed surface (mm$^2$) illustrates the method for adjusting the total exposed surface (i.e., the active surface) according to the diameter of the coating of adhesive PU. The figures in this chart are for a length of 40 mm for a three strand microcable of overall diameter 0.3 mm.

This variant makes it possible to further optimize the use of the active surface of the electrode of the microcable, promoting its longitudinal extension. Note that the exhibited helical regions 50, 50', 50'' may, if desired, occur only on some parts of the microcable, for example, by alternating active regions where the helical exposed surfaces are apparent and completely isolated regions, e.g. by means of PU tubes such as the tubes 44 described with reference to the first embodiment described above.

Furthermore, the bare conductive areas of the microcable may receive a porous coating, such as NiTi, or be coated with an additional layer formed by a carbon film deposited by sputtering, to improve the biocompatibility properties between the microcable, its insulation and its environment, in order to avoid degradation of the parts in contact with the blood flow. The U.S. Pat. No. 5,370,684 A and U.S. Pat. No. 5,387,247 A, issued to Sorin Biomedica SpA, describe sputtering a submicron thin carbon film, on implantable prostheses such as catheters, heart valves, etc., in polyurethane or in silicone. These documents are to be referred to for more details on the technology to make this carbon film deposit, which are incorporated herein by reference.

Figure 6:
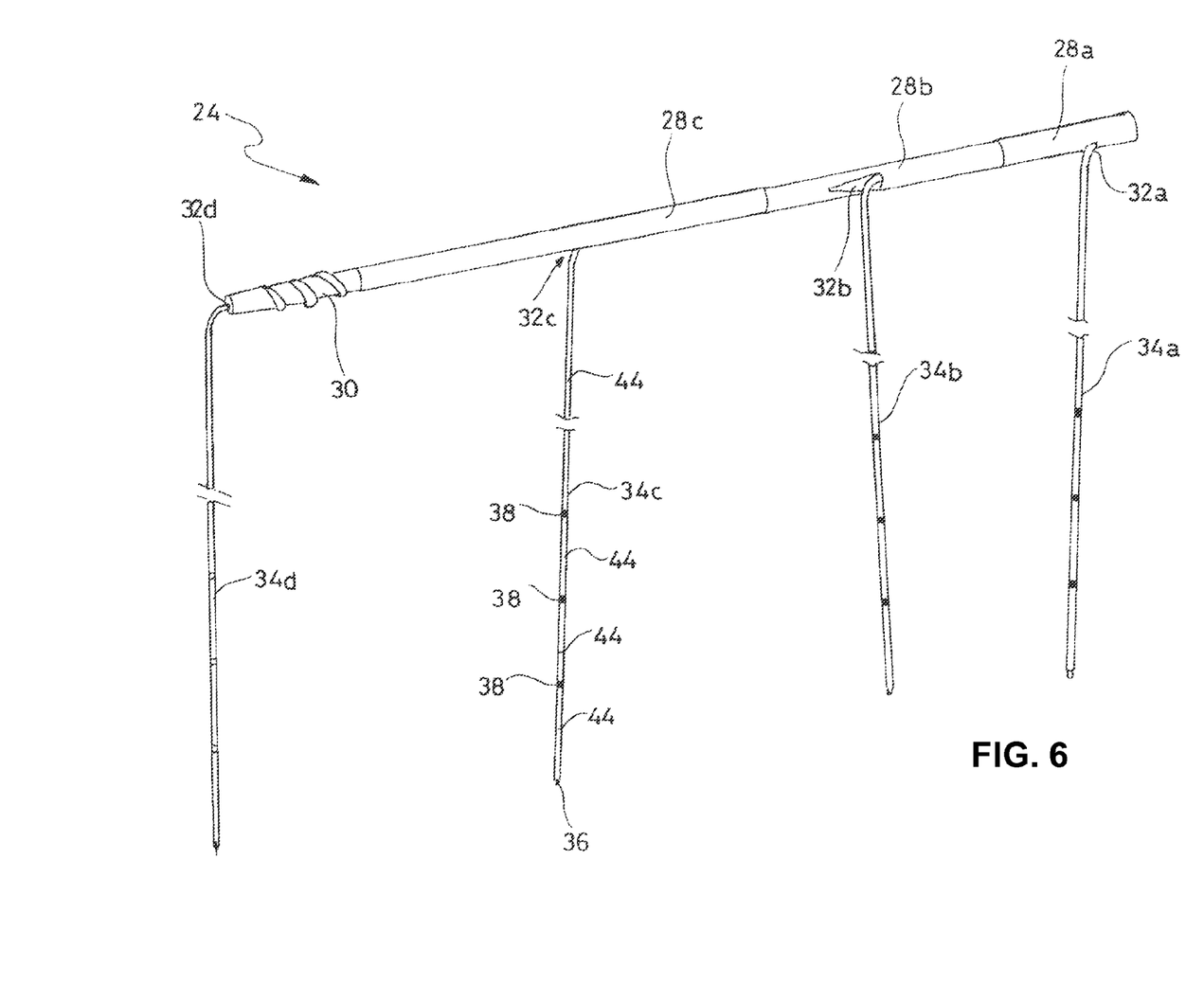
FIG. 6 illustrates a third embodiment of the invention, wherein the lead carries a plurality of separate microcables.

FIG. 6 shows a third embodiment of the present invention, which is a variant of the first embodiment, wherein the lead carries a plurality of separate microcables, each of which being similar to that described above and shown in FIGS. 2 and 3. In this embodiment, a single lead body 24 is equipped with several internal parallel lumens from which a plurality of respective microcables laterally emerges.

Thus, in FIG. 6, the lead body comprises a plurality of sections 28a, 28b, 28c, each provided with an opening 32a, 32b, 32c communicating with a respective lumen. It also includes at its distal end retaining means 30 and the hole 32d.

Out of each of the holes 32a, 32b, 32c, 32d emerges a respective microcable 34a, 34b, 34c, 34d, made according to either of the embodiments described above, for example, according to the first embodiment in the example shown in FIG. 6. Each of these microcables includes its own network of electrodes 36, 38 electrically joined together and separated by insulating parts 44, on the entire length of the emerging part.

This solution allows covering a large area of the left ventricle, with a multitude of electrodes connected in parallel, each branch corresponding to each active portion 34a, 34b, 34c, 34d remaining however, electrically independent thanks to its own electrical connection to the proximal end of the lead. This link allows connection to a corresponding terminal of a multi-connector head, for example, of the 18-4 type. Also, a multiplexing system may be included inside the lead to separately handle connecting the different electrode arrays.

In general, whatever embodiment is employed, the technique just described has many advantages, among which include, in particular:

simplified method of implantation, requiring only conventional equipment;
stability of the electrical contact with the tissue regardless of the size of the vein;
possibility of extending the usable portion of the vein, including the distal area to the venous system, with an excellent adaptation to the thin venous networks, while maintaining an attachment point to the target vein (at the retaining means 30);
effective distribution of the electrical flow in the deep regions of the epicardium;
high reliability as a result of the mechanical performances of the nitinol structure of the microcable;
overall mechanical simplicity, therefore having a low manufacturing cost and high reliability;
radiopacity, based on the platinum core of each strand forming the microcable as well the platinum rings (in the case of the first embodiment);
easy extraction, thanks to (i) the isodiametric profile of the microcable, (ii) its small diameter, and (iii) to its high tensile strength (one-piece robust structure of the microcable at its end); for the lead body, it is sufficient to simply unscrew the distal end of the lead body at the level of retaining means 30 before removing the lead body.

One skilled in the art will appreciate that the present invention can be practiced by other than the embodiments described herein, which are provided for purposes of illustration and not of limitation.

The invention claimed is:

1. A pacing lead, comprising:
    at least one microcable comprising a plurality of distinct bare areas which form a network of stimulation electrodes electrically connected together;
    the microcable comprising a plurality of strands twisted together;
    each of the plurality of strands comprising:

a metallic core to provide stimulation; and a radiopaque sheath surrounding the metallic core;

wherein the distinct bare areas that form the network of stimulation electrodes are provided on outward-facing portions of at least some of the plurality of strands; and wherein a proximal end of the lead is configured to be coupled to a generator of an active implantable medical device.

2. The lead of claim 1, wherein the plurality of strands form a microcable system, and wherein the system is coated with an insulating layer.

3. The lead of claim 1, wherein a distal end of the microcable comprises a pre-formed shape having at least two dimensions for anchoring to tissue.

4. The lead of claim 1, further comprising a lead body comprising a hollow sheath made of a deformable material and with a central lumen open at both ends, wherein at least a portion of the at least one microcable is slidably disposed in and spans the entire length of the lead body, and wherein a portion of the at least one microcable emerges beyond a distal end of the lead body.

5. The lead of claim 4, wherein the distal end of the lead body further comprises a helical relief having a thread wrapping at least part way around the lead body.

6. The lead of claim 4, wherein the lead further comprises:

a plurality of distinct telescopic microcables housed in the lead body and sliding therein, each said microcable emerging from the lead body in separate locations longitudinally spaced along the lead body.

7. The lead of claim 1, wherein the plurality of distinct bare regions of the microcable comprises an exposed total surface area of at least 1 mm².

8. The lead of claim 1, wherein the plurality of distinct bare regions extend in succession along the microcable.

9. The lead of claim 8, wherein the distinct bare areas are separated from each other by portions of a tube made of an electrically nonconductive material, wrapping and sheathing the microcable between two consecutive bare areas.

10. The lead of claim 1, wherein the distinct bare regions bear tubular rings made of an electrically conductive material, crimped on the microcable.

11. The lead of claim 1, wherein the microcable comprises a multi-wire structure coated with an insulating material, in which the distinct bare areas are formed by ablation of the insulating material along the microcable.

12. The lead of claim 1, wherein the microcable comprises at least one bare helical area extending along the microcable.

13. The lead of claim 12, wherein at least a portion of the microcable comprises a strand formed of a plurality of twisted strands having a corresponding plurality of bare helical regions isolated from each other in the circumferential direction by helical coatings of electrically non-conductive material.

14. The lead of claim 1, wherein the lead is configured for implantation in a coronary vein system for the stimulation of a left cavity of a heart.

15. The lead of claim 1, wherein the microcable comprises a diameter between 0.5 and 2 French.

16. The lead of claim 1, wherein the bare areas have a porous coating.

17. The lead of claim 1, wherein the bare areas comprise a plurality of holes communicating with a respective lumen.

18. The lead of claim 17, wherein a microcable extends out of each hole and includes a network of electrodes.

19. The lead of claim 18, wherein the network of electrodes for each microcable is connected in parallel.

20. The lead of claim 17, wherein one of the holes is located at the distal end of the lead.

* * * * *